United States Patent
Giffels et al.

(12) 
(10) Patent No.: US 6,296,788 B1
(45) Date of Patent: Oct. 2, 2001

(54) PROCESS FOR THE PREPARATION OF GRIGNARD REAGENTS AND NOVEL GRIGNARD REAGENTS

(75) Inventors: Guido Giffels, Bonn; Guido Steffan, Odenthal, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/615,434

(22) Filed: Jul. 13, 2000

(30) Foreign Application Priority Data

Jul. 20, 1999 (DE) ............................................. 199 33 833

(51) Int. Cl.$^7$ ....................................................... C07F 3/02
(52) U.S. Cl. ........................................................ 260/665 G
(58) Field of Search ........................................ 260/655 G

(56) References Cited

U.S. PATENT DOCUMENTS

| | | | | |
|---|---|---|---|---|
| 2,921,940 | * | 1/1960 | Ramsden | 260/665 G |
| 5,827,887 | | 10/1998 | Gourvest et al. | 514/563 |
| 6,117,372 | | 9/2000 | Bogdanović et al. | 260/665 G |
| 6,221,285 | * | 4/2001 | Bogdanovic et al. | 260/665 G |

OTHER PUBLICATIONS

Tetrahedron Lett. (1993), 34 (50), 8063–8066, XP000941010, Sharon Real et al, "A Novel and Highly Efficient Desymmetrization of a Meso–Anhydride by a Chiral Grignard Reagent".

Tetrahedron, Bd. 55, Mar. 8, 1999, 2889–2898, XP000919007, A Orita et al "Integrated Chemical Process".

J. Am. Chem. Soc., 77 (month unavailable) 1955, p. 1114–1116, S. V. Lieberman, "The Use of the Disproportionation of Esters of 2–Propanenitronic Acid to Convert Halides to Carbonyl Compounds and Benzaldehyde to Benzamides".

Synthesis, Jul. 1993, pp. 705–713 R. Sakoda et al "Novel Synthesis of α–Acetylstyrylphosphonates".

J. Am. Chem. Soc., 71, Jun., 1949, pp. 2271–2272, New Compounds, Ronald A. Henry et al. "Some Derivatives of Morpholine".

Chem. Ber., 123, (Month unavailable) 1990, pp. 1841–1843, H. Feulner et al "Darstellung und Strukturelle Charakterisierung der p–Formylbenzolboronsäure".

* cited by examiner

Primary Examiner—Jean F. Vollano
(74) Attorney, Agent, or Firm—Joseph C. Gil; Richard E. L. Henderson

(57) ABSTRACT

Grignard reagents which contain a protected aldehyde function are obtained in a particularly advantageous manner from a halogenated aldehyde by reaction with a secondary monoamine to give an open-chain aminal, and conversion of the latter into a Grignard reagent using metallic magnesium. The invention also relates to novel Grignard reagents of this type.

10 Claims, No Drawings

PROCESS FOR THE PREPARATION OF GRIGNARD REAGENTS AND NOVEL GRIGNARD REAGENTS

The present invention relates to a process for the preparation of Grignard reagents which contain a protected aldehyde function, and to novel Grignard reagents of this type.

Grignard reagents are important intermediates in organic synthesis, which enable various types of functional groups to be introduced into a molecule. Numerous active ingredients can be prepared in this way.

The conversion of a starting compound into a Grignard reagent is not, however, directly possible in every case. There are functional groups, e.g. the aldehyde function, which are incompatible with a grignardization. If such a functional group is present in the molecule and if it is to be retained during a Grignard synthesis step, then this group must be protected by suitable chemical derivatization. Then, following the Grignard synthesis step, this derivatization must be reversed and the original functional group restored. For this reason, prior to Grignard reactions, aldehyde groups are usually converted into acetals by reaction with alcohols or ortho esters, and these acetals are later cleaved again by acidic hydrolysis. Thus, 4-bromo-benzaldehyde, protected e.g. as diethyl acetal, is reacted, following conversion into the Grignard reagent by reaction with tributyl borate, to give 4-formyl-benzeneboronic acid (Chem. Ber. 123, 1841–1843 (1990)), which is of economic interest as the synthesis building block for constructing biaryl backbones for pharmaceutical active ingredients (EP-A 757 982).

Recently, a process has been described which can be used to convert chloroaromatics into Grignard reagents (WO 98/02443). However, chloroaromatics are less reactive than bromoaromatics, meaning that conversion of chloroaromatics into Grignard reagents is often not directly possible. In the process of WO 98/02443, an inorganic Grignard reagent of a transition metal is therefore additionally used as catalyst. This process is generally applied to chloroaromatics which are free from aldehyde groups.

Only in the document of WO 98/02443 (Example 16 therein) is a grignardization of 2-(4-chloro-phenyl)-1,3-imidazolidine described which has been prepared from p-chlorobenzaldehyde and N,N'dibenzylethylenediamine. The grignardization and the subsequent stage prepared therefrom were obtained in good yields. A disadvantage of this synthesis route is the use of a dialkylated ethylenediamine as protective group. Diamines of this type are very expensive compared with other protective groups and are not directly obtainable in industrial amounts. Also, the protective group remains in the molecule following the reaction and has to be removed in a further, complex reaction step.

Attempts have therefore been made to carry out this process using a customary protective group for the aldehyde function, where, firstly, p-chlorobenzaldehyde is reacted with triethyl orthoformate to give p-chlorobenzaldehyde diethyl acetal, and this was subjected to grignardization. However, only about 34% of the p-chlorobenzaldehyde diethyl acetal was converted into the Grignard reagent (see Comparative Example 1). The reaction of p-chlorobenzaldehyde with 1,3-propanediol to give 2-(4-chloro-phenyl)-1,3-dioxolane did not give a usable route to Grignard reagents of p-chlorobenzaldehyde either since the dioxolane proved to be incapable of undergoing a grignardization (see Comparative Example 2). From this it can be concluded that acetal protective groups are unsuitable for the conversion of chloroaromatics into Grignard reagents by the process of WO 98/02443.

There therefore continues to be a need for a process for the preparation of Grignard reagents which contain a protected aldehyde function in which it is possible to start from not only bromine-containing, but predominantly also from chlorine-containing, aldehydes, and in which protective groups can be used which are low cost, available in industrial amounts and can be cleaved off again in a simple manner.

We have now found a process for the preparation of Grignard reagents which contain a protected aldehyde function which is characterized in that, firstly, a halogenated aldehyde is reacted with a secondary monoamine to prepare an open-chain aminal, and the latter is converted into a Grignard reagent using metallic magnesium.

For the process according to the invention, suitable secondary monoamines are, for example, those of the formula (I)

in which $R^1$ and $R^2$ are identical or different and are each a straight-chain or branched $C_1$–$C_{10}$-alkyl or alkylene, or a $C_6$–$C_{10}$-aryl which is optionally substituted by up to 3 $C_1$–$C_4$-alkyl radicals and cyclic amines of the formula

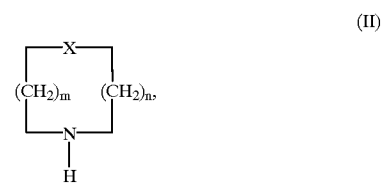

in which m and n independently of one another are zero, 1 or 2, and the sum m+n is at least 1, and X is oxygen or a $CH_2$ group.

Preference is given to amines of the formula (I) in which $R^1$ and $R^2$ are identical and are a straight-chain $C_1$–$C_4$-alkyl or phenyl, and to cyclic amines of the formula (II) in which m and n are each 2.

Particularly preferred amines are dimethylamine and morpholine.

The secondary monoamine, in particular secondary alkylamines, can optionally be used as aqueous solution, preferably in concentrated aqueous solution.

For the process according to the invention, suitable halogenated aldehydes are, for example, straight-chain or branched $C_2$–$C_{25}$-alkyl aldehydes containing 1 to 3 halogen atoms, and $C_6$–$C_{10}$-aryl aldehydes containing 1 to 3 halogen atoms. The halogen atoms can, for example, be chlorine, bromine and/or iodine, preference being given to chlorine and/or bromine, particular preference being given to chlorine. Preferably, only one halogen atom is present in the halogenated aldehydes. As halogenated aldehydes, benzaldehydes are preferred, in particular chlorobenzaldehydes and very particularly p-chlorobenzaldehyde.

The preparation of the open-chain aminal from the halogenated aldehyde and the secondary monoamine can be carried out in a manner known per se (see e.g. J. Am. Chem. Soc. 77, 1114–1116 (1955) and 71, 2271–2272 (1949) and Synthesis 1993, 705–713) or analogously thereto. A possible procedure can, for example, involve using at least 2 mol, preferably 2.1 to 5 mol, of secondary monoamine per mole of halogenated aldehyde, and azeotropically distilling off the water of reaction formed either with a suitable solvent, or removing it using a water-abstracting agent (for example potassium carbonate or boric anhydride).

Suitable reaction temperatures are, for example, those in the range −30 to +150° C. The open-chain aminal prepared can be isolated in various ways, e.g. by extraction, distillation or crystallization.

For clarification, it is pointed out that the term "open-chain aminals" means aminals in which the two nitrogen atoms are not bridged to one another. For example, the formula (III) shows an open-chain aminal, whereas the formula (IV) shows a bridged aminal.

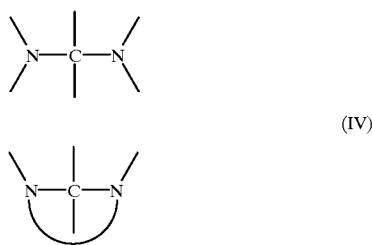

(III)

(IV)

The conversion into the Grignard reagent is carried out by reacting the open-chain aminal with metallic magnesium. In the case of the more reactive open-chain aminals, in which the grignardization takes place at a bromine or iodine atom, it is possible to proceed by methods known per se for the preparation of Grignard reagents (see e.g. Organikum, 16$^{th}$ Edition, VEB Deutscher Verlag der Wissenschaften, Berlin 1986, p. 495 et seq.). In the process, the open-chain aminal can, for example, be reacted at a temperature of from −20° C. up to the boiling point of the solvent or solvent mixture, preferably between 0 and 100° C., with magnesium turnings or magnesium powder in an ether as solvent or in a mixture of an ether and a hydrocarbon as solvent. Suitable ethers are, for example, tetrahydrofuran, 2-methyltetrahydrofuran, diethyl ether, tert-butyl methyl ether and dimethoxyethane, suitable hydrocarbons are, for example, toluene, cyclohexane, hexane and heptane. Preference is given to using tetrahydrofuran or tetrahydrofuran/toluene mixtures. In the case of open-chain aminals in which the grignardization takes place at a chlorine atom, it may be necessary to activate the magnesium catalytically, e.g. in the manner described in WO 98/02443.

The magnesium can be used, for example, in the form of the turnings commercially available for Grignard reactions, or as powder and, for example, in an excess of from 1.05 to 2 mol equivalents, based on the halogen compound. Suitable activators for initiating the reaction are, for example, elemental iodine or lower bromoalkanes, preferably bromoethane or 1,2-dibromoethane. The preparation of the Grignard reagent is generally carried out in a controlled metered manner by adding the halogen compound at temperatures between 0° C. and the boiling temperature of the solvent and optionally a postreaction. The resulting solution or suspension of the Grignard reagent can—optionally following removal of excess magnesium—be used in the next stage without further work-up.

The preparation of the Grignard reagent is usually followed, as the next reaction step, by its reaction with an electrophilic reagent. Possible electrophiles are, for example, epoxides, acid chlorides, esters, boric esters, amides, anhydrides and trialkylchlorosilanes, and molecules containing C=X multiple bonds, such as aldehydes, ketones or nitrites (see e.g. Handbook of Grignard Reagents, Marcel Dekker Verlag, N.Y., 1996, Part VI).

Just as easy as the synthesis is the cleavage of the open-chain aminals after the reaction of the Grignard reagent has taken place, with back-formation of the aldehyde function. If, during the hydrolytic work-up following the reaction of the Grignard reagent with an electrophilic reagent in the water phase, a weakly acidic pH of e.g. 5 to 1 is set, the aminals are cleaved directly and completely. In this connection, it is very advantageous not only that the work-up of the reaction mixture and the cleavage of the protective group take place in a single step, but also that the eliminated amines accumulate in the weakly acidic water phase, whereas the desired reaction product is normally in the organic phase. In this manner, it is possible to carry out removal of the product from the reaction mixture and removal of the protective group from the product at the same time.

Accordingly, the open-chain aminals satisfy, in a virtually ideal manner, the requirements which are placed on a protective group: they are low-cost, easy to attach and easy to remove, and the desired synthesis can be carried out with the protected compound in good yield. Using such a protective group, it is even possible to quantitatively convert the protected p-chlorobenzaldehyde into the corresponding Grignard reagent without specific activation, as is described in WO 98/02443.

It is extremely surprising that these advantages can be achieved using the process according to the invention since the open-chain aminals are sufficiently stable even under the sometimes very drastic conditions of the grignardization. This stability was not to be expected since open-chain aminals lack the stabilizing action of the heterocyclic ring which is present in the case of the known bridged aminals.

In the process according to the invention, recovery of the secondary monoamines used for the formation of the open-chain aminals is superfluous since these chemicals are available at low cost. In the case of the known processes using symmetrical ethylenediamines and the formation of bridged aminals as protective group, this is not possible since here the symmetrical ethylenediamines have to be recovered for reasons of cost.

Using the process according to the invention, it is possible, in a particularly good manner, to convert 4-chlorobenzaldehyde into the corresponding open-chain aminal and to convert the latter virtually quantitatively into a corresponding Grignard reagent. Good yields were also realized in the reactions of this Grignard reagent in a variety of subsequent stages.

A number of the Grignard reagents which can be prepared by the process according to the invention are novel. The present invention therefore also relates to Grignard reagents of the formulae (V) and (VI)

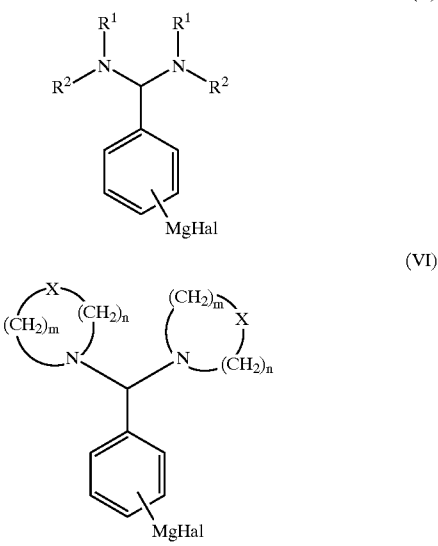

in which
R¹ and R² have the same meanings as in formula (I), and
m, n and X have the same meanings as in formula (II), and
Hal is chlorine or bromine.

Preferred compounds of the formulae (V) and (VI) are those in which the symbols used have the preferred meanings given in formula (I) and in formula (II) respectively.

Particularly preferred Grignard reagents according to the invention are 4-(di-(di-methylamino)-methyl)-phenylmagnesium chloride and 4-(dimorpholinomethyl) phenylmagnesium chloride.

Processes for the preparation of the Grignard reagents according to the invention and their use are described in more detail above and in the examples, as are the technical advances achievable therewith.

If desired, the compounds of the formulae (V) and (VI) can be isolated, e.g. by filtration of the crystalline precipitate which is formed during cooling of the reaction mixture in their preparation. These compounds are generally re-used in the form of the reaction mixture which forms during their preparation, optionally following removal of excess magnesium and optionally following dilution with a suitable solvent.

EXAMPLES

All reactions for the preparation and reaction of Grignard reagents were carried out with dry tetrahydrofuran (water content below 0.02% by weight) and under argon as protective gas.

Example 1
1-Chloro-4-(dimorpholinomethyl)-benzene 70 g of p-chlorobenzaldehyde and 105 g of morpholine were heated to boiling in 260 g of methylcyclohexane in a water separator. Over the course of 45 minutes, 8.4 ml of water were removed azeotropically. The mixture was left to cool with slow stirring. At 58° C., the solution was seeded, and very fine crystals slowly precipitated out. The mixture was cooled in an ice bath to +5° C. After a post-stirring time of 1 hour, the solid which had precipitated out was filtered off with suction. The white product was washed with 2×50 ml of methylcyclohexane and dried overnight in a drying cabinet at 20° C. and 100 mbar. 129.2 g of product were obtained in the form of white crystals (87% of theory).

In an analogous manner, 1-bromo-4-(dimorpholino)-benzene was obtained in 94% yield from 4-bromobenzaldehyde and morpholine using cyclohexane as solvent.

Example 2
1-Chloro-4-(di-(dimethylamino)-methyl)-benzene 373 g of a 60% strength by weight aqueous dimethylamine solution were added to 291 g of 4-chlorobenzaldehyde. The mixture was heated to 50° C. during which all of the solid dissolved, and was stirred for 3 hours at 50–55° C. The temperature was then increased to 100° C. (bath temperature) for 15 minutes. The mixture was slowly left to cool to room temperature for 2.5 hours with stirring. 150 g of potassium carbonate were then added to the resulting reaction mixture, the upper organic phase was separated off after the addition of 450 ml of petroleum ether, and the aqueous phase was extracted with 100 ml of toluene. The combined organic phases were dried over potassium carbonate, the solvent was distilled off, and the residue was fractionally distilled under reduced pressure. The product distilled over at 80° C. and 0.8 mbar. 345.4 g of product were obtained in the form of a yellowish oil (=78% of theory).

Example 3
4-(Di-(dimethylamino)-methyl)-phenylmagnesium chloride 4 g of magnesium powder (Ø below 0.1 mm) in 20 ml of tetrahydrofuran were activated at 60° C. using 0.25 ml of bromoethane. Then, 26.59 g of 1-chloro-4-(di-(dimethylamino)-methyl)-benzene (obtained as in Example 2) in 80 ml of tetrahydrofuran were added dropwise over one hour, and the mixture was then stirred for a further 4 hours at 60° C. During cooling, some of the Grignard reagent precipitated out.

To monitor the metalation, a sample was taken from the resulting suspensions of the Grignard reagent and hydrolysed with aqueous 1 M hydrochloric acid, the aqueous phase was separated off and extracted with tert-butyl methyl ether, and the combined organic phases were dried with $Na_2SO_4$ and analysed using GC. The Grignard reagent is converted in this manner into benzaldehyde, whilst unreacted aminal is cleaved back to give chlorobenzaldehyde. In the GC analysis, only benzaldehyde was found, which indicates complete metalation.

Example 4
4-(Di-(dimethylamino)-methyl)-phenylmagnesium bromide 4 g of magnesium turnings were covered with 20 ml of tetrahydrofuran, and an iodine crystal was added. Then, at 23° C., the dropwise addition of a solution of 42.66 g of 1-bromo-4-(di-(dimethylamino)-methyl)-benzene in 80 ml of tetrahydrofuran was started. After 20 ml of the solution had been added, the mixture was heated to 60° C. and a few drops of bromoethane were added, as a result of which the reaction started. The remaining solution was added dropwise with occasional cooling such that the temperature remained at about 40° C. When the metered addition was complete, the cooling bath was removed, as a result of which the temperature increased again to 58° C., and the mixture was subsequently stirred for a further 1 h, during which some of the Grignard reagent gradually precipitated out as a fine orange precipitate. To complete the metalation, the mixture was then stirred for a further hour at 50° C. In the GC analysis of a hydrolysed sample, only benzaldehyde was found which, as explained in Example 3, means complete metalation.

As a result of the conversion into the Grignard reagent, the $^1$H-NMR signal for the aromatic protons of the aminal at 7.45 ppm (doublet, $^3J_{HH}$=8 Hz, measured in $^1$H-THF against D$_2$O standard in extracapillary) shifts to 7.0 ppm. The $^1$H-NMR signal at 7.8 ppm (doublet, $^3J_{HH}$ about 6.5 Hz) remains virtually unchanged. Measurements were taken from the supernatant Grignard solution in $^1$H-THF.

Example 5
4-(Dimorpholinomethyl-phenylmagnesium chloride

Analogously to Example 3, 3.35 g of magnesium powder in 20 ml of tetrahydrofuran were activated using 0.25 ml of bromoethane and then, at 40° C. with vigorous stirring, 375 mg of anhydrous iron(II) chloride were added. After 40 minutes, the mixture was heated to 60° C. and then 37.1 g of 1-chloro-4-(dimorpholinomethyl)benzene (obtained as in Example 1) in 85 ml of tetrahydrofuran were added dropwise over the course of 80 minutes. The mixture was then stirred for a further 3.5 hours. The GC analysis of a hydrolysed sample revealed 91.1 area % of benzaldehyde and 3.1 area % of 4-chlorobenzaldehyde. Metalation had therefore taken place virtually completely.

Example 6
4-Trimethylsilylbenzaldehyde

A solution of 19.5 ml of trimethylchlorosilane in 50 ml of tetrahydrofuran was added dropwise over 35 minutes, with ice cooling at 20 to 28° C., to the Grignard reagent suspension obtained as in Example 5. The mixture was left to warm to room temperature and then stirred for 16 hours. The resulting black solution was slowly hydrolysed with 50 ml of iced water, and then adjusted to a pH of 4.5 using 60 g of aqueous 2 M sulphuric acid. The phases which form were separated and the aqueous phase was extracted with 3×50 ml of tert-butyl methyl ether. The combined organic phases were washed with 100 ml of saturated aqueous sodium chloride solution, and the solvent was distilled off. 22.1 g of a red-brownish oil were obtained, which, according to GC-MS, had a content of 96% of 4-trimethylsilylbenzaldehyde, corresponding to a yield of 95% of theory.

Example 7
4-Formylbenzeneboronic acid

The Grignard reagent obtained as in Example 3 was completely dissolved in 85 ml of dimethoxyethane, decanted off from the excess magnesium and placed in a dropping funnel. The solution was added dropwise over the course of 40 minutes, at the same time as a solution of 14 ml of trimethyl borate in 5 ml of tetrahydrofuran, into a flask thermostatted at −60° C., to which 14 ml of tetrahydrofuran had been charged. The cooling bath was then removed and the mixture was stirred for a further 1 hour. The resulting paste was hydrolysed with 121 g of 2-molar aqueous sulphuric acid. When the reaction mixture no longer contained any solid constituents, the organic phase was separated off and concentrated to ⅓ by distilling off the solvent, and the product was precipitated out therefrom with stirring by the addition of 280 g of 1-molar hydrochloric acid. Filtering gave 13.6 g of product in the form of a pale yellow powder, which, according to HPLC, had a content of 96% by weight, corresponding to a yield of 70% of theory.

Example 8
1-(4-Formylphenyl)butan-1-ol

A solution of 9 g of butyraldehyde in 50 ml of tetrahydrofuran was added dropwise over 40 minutes at 15° C. to a Grignard reagent suspension obtained as in Example 5. The mixture was then left to warm to room temperature and then stirred for 16 hours. The reaction mixture was then, with ice cooling, firstly hydrolysed with 50 ml of water and then adjusted to a pH of 3 using 122 g of aqueous 2 M sulphuric acid. The organic phase was separated from the aqueous phase, the aqueous phase was extracted with 2×50 ml of tert-butyl methyl ether, and the organic phases were combined, washed with 100 ml of saturated aqueous sodium chloride solution and dried with sodium sulphate. Distilling off the solvent gave the product in the form of 21.56 g of a reddish oil. According to GC, it had a content of 62 area %, which corresponds to a yield of 60% of theory.

Comparative Example 1

Grignardization of p-chlorobenzaldehyde Diethyl Acetal 6.5 g of magnesium powder in 20 ml of tetrahydrofuran were activated with 0.5 ml of bromoethane, and 750 mg of Fe(II) Cl$_2$ (anhydrous) were added at 50° C. with vigorous stirring. After 1.5 hours, 56.67 g of 4-chlorobenzaldehyde diethyl acetal in 150 ml of tetrahydrofuran were added dropwise over the course of 2.5 hours, and the mixture was then stirred for a further 3 hours at 50° C. The GC analysis of a hydrolysed sample revealed a content of 34% of benzaldehyde and 58% of 4-chlorobenzaldehyde. This means: only 34% of the feed material had undergone a grignardization.

Comparative Example 2

Grignardization of 2-(4-chlorophenyl)-1,3-dioxolane

In the experiment to metallate 2-(4-chlorophenyl)-1,3-dioxolane in a manner comparable with that in Comparative Example 1, it was not possible to obtain the Grignard compound. GC analysis of a hydrolysed sample revealed only 0.1% of benzaldehyde.

What is claimed is:

1. A process for preparing Grignard reagents which contain a protected aldehyde function comprising (a) reacting a halogenated aldehyde with a secondary monoamine to prepare an open-chain aminal, and (b) converting the open-chain aminal into a Grignard reagent using metallic magnesium.

2. A process according to claim 1, wherein the secondary monoamine has the formula (I)

(I)

wherein

R$^1$ and R$^2$ are identical or different and are each a straight-chain or branched C$_1$–C$_{10}$-alkyl or alkylene, or a C$_6$–C$_{10}$-aryl that is optionally substituted by up to 3 C$_1$–C$_4$-alkyl radicals, or the formula (II)

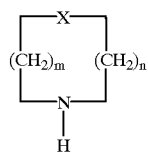

(II)

wherein m and n independently of one another are zero, 1 or 2, and the sum m+n is at least 1, and X is oxygen or a $CH_2$ group.

3. A process according to claim 1, wherein the halogenated aldehyde is a straight-chain or branched $C_2$–$C_{25}$-alkyl aldehyde containing 1 to 3 halogen atoms or a $C_6$–$C_{10}$-aryl aldehyde containing 1 to 3 halogen atoms.

4. A process according to claim 1, wherein the halogenated aldehyde is a chloro- or bromobenzaldehyde.

5. A process according to claim 1, wherein for the preparation of the open-chain aminals at least 2 mol of secondary monoamine are used per mole of halogenated aldehyde, the reaction is carried out at −30 to +150° C., and the water of reaction formed is separated off.

6. A process according to claim 1, wherein the conversion into the Grignard reagent is carried out by reacting the open-chain aminal with metallic magnesium at a temperature of −20° C. up to the boiling point of the solvent, and using as solvent an ether or a mixture of an ether and a hydrocarbon.

7. A process according to claim 1, wherein an excess of from 1.05 to 2 equivalents of magnesium, based on the halogen compound, are used.

8. A process according to claim 1, wherein an activator used for initiating the reaction for the preparation of the Grignard reagent is elemental iodine or a lower bromoalkane.

9. A Grignard reagent of the formula (V)

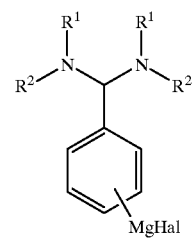

(V)

wherein $R^1$ and $R^2$ are identical or different and are each a straight-chain or branched $C_1$–$C_{10}$-alkyl or alkylene or a $C_6$–$C_{10}$-aryl that is optionally substituted by up to 3 $C_1$–$C_4$-alkyl radicals, and Hal is chlorine or bromine.

10. A Grignard reagent of the formula (VI)

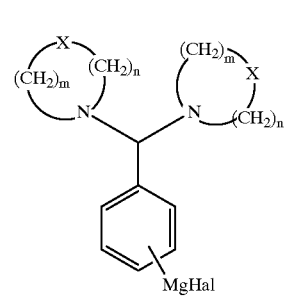

(VI)

wherein m and n independently of one another are zero, 1, or 2, and the sum m+n is at least 1, X is oxygen or a $CH_2$ group, and Hal is chlorine or bromine.

* * * * *